US00PP18367P2

(12) United States Plant Patent
van der Zwet

(10) Patent No.: US PP18,367 P2
(45) Date of Patent: Dec. 25, 2007

(54) ***MONARDA* PLANT NAMED 'PINK LACE'**

(50) Latin Name: *Monarda didyma*
Varietal Denomination: Pink Lace

(75) Inventor: Alexius Joannes Joseph van der Zwet, Oude Wetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/499,637

(22) Filed: Aug. 5, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Monarda* plant named 'Pink Lace', characterized by its compact, upright and outwardly spreading plant habit; basal branching habit; freely flowering habit; and red purple-colored flowers.

2 Drawing Sheets

Botanical designation: *Monarda didyma.*
Cultivar denomination: 'Pink Lace'.

BACKGROUND OF THE INVENTION

The present invention relates to a new and distinct cultivar of *Monarda,* botanically known as *Monarda didyma* and hereinafter referred to by the name 'Pink Lace'.

The new *Monarda* originated from an open-pollination of an unnamed selection of *Monarda didyma,* not patented, as the female, or seed, parent with an unknown selection of *Monarda didyma,* as the male, or pollen, parent. The new *Monarda* was discovered and selected by the Inventor as a single flowering plant from within the progeny of the stated open-pollination grown in a controlled environment in Oude Wetering, The Netherlands in 2002.

Asexual reproduction of the new cultivar by softwood cuttings in Oude Wetering, The Netherlands, since 2003, has shown that the unique features of this new *Monarda* are stable and reproduced true to type in successive generations.

SUMMARY OF THE INVENTION

Plants of the cultivar Pink Lace have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Lace'. These characteristics in combination distinguish 'Pink Lace' as a new and distinct cultivar:

1. Compact, upright and outwardly spreading plant habit.
2. Basal branching habit.
3. Freely flowering habit.
4. Red purple-colored flowers.

Plants of the new *Monarda* differ from plants of the female parent selection primarily in plant size and flower color.

Plants of the new *Monarda* can be compared to plants of the Monarda cultivar Twins, not patented. In side-by-side comparisons conducted by the Inventor in Oude Wetering, The Netherlands, plants of the new *Monarda* differed from plants of the cultivar Twins in the following characteristics:

1. Plants of the new *Monarda* were more compact than plants of the cultivar Twins.
2. Flower color of plants of the new *Monarda* was brighter than flower color of plants of the cultivar Twins.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Monarda.*

The photograph on the first sheet is a side perspective view of a typical plant of 'Pink Lace' grown in a container.

The photograph at the top of the second sheet is a close-up view of a typical flower of 'Pink Lace'.

The photograph at the bottom of the second sheet is a close-up view of a typical leaf of 'Pink Lace'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the summer in an outdoor nursery in Lisserbroek, The Netherlands for about two years. During the production of the plants, day temperatures ranged from 14° C. to 32° C. and night temperatures ranged from 7° C. to 14° C.

Botanical classification: *Monarda didyma* cultivar Pink Lace.

Parentage:

*Female parent.*—Unnamed selection of *Monarda didyma,* not patented.

*Male parent.*—Unknown selection of *Monarda didyma,* not patented.

Propagation:

*Type cutting.*—Softwood cuttings.

*Time to produce a rooted young plant.*—About two to three months at 18° C.

*Root description.*—Fine, fibrous; light brown to white in color.

*Rooting habit.*—Freely branching; moderately dense.

Plant description:

*Form.*—Perennial. Compact, upright and outwardly spreading plant form; broad inverted triangle; basal branching habit. Moderately vigorous growth habit. Single flowers arranged on globular spikes.

*Plant height.*—About 45 cm.

*Plant width.*—About 43 cm.

*Lateral branch description.*—Length: About 19.6 cm. Diameter: About 3 mm. Internode length: About 8.8 cm. Strength: Strong. Aspect: Upright. Texture: Sparsely pubescent. Color: 137A to 138A.

Foliage description:

*Arrangement.*—Opposite, simple.

*Length.*—About 8.7 cm.

*Width.*—About 3.8 cm.

*Shape.*—Ovate.

*Apex.*—Apiculate.

*Base.*—Obtuse to cordate.

*Margin.*—Serrate.

*Texture, upper and lower surfaces.*—Pubescent.

*Venation pattern.*—Pinnate.

*Color.*—Developing foliage, upper surface: 141A. Developing foliage, lower surface: 137C to 137D. Fully expanded foliage, upper surface: 131A to 139A; venation, 144B. Fully expanded foliage, lower surface: 137C; venation, 145B to 145C.

*Petiole length.*—About 1.4 cm.

*Petiole diameter.*—About 2 mm.

*Petiole color, upper surface.*—183D.

*Petiole color, lower surface.*—145A.

Flower description:

*Flower arrangement and shape.*—Single labiate flowers arranged in terminal globular spikes; flowers face outwardly. Flowers sessile. Freely flowering, about 350 flowers per lateral branch. Natural flowering season: Continuous flowering from late July to late August in The Netherlands.

*Flower longevity on the plant.*—About five days; flowers not persistent.

*Fragrance.*—Moderate; spicy, pleasant.

*Flower buds.*—Length: About 1.9 cm. Diameter: About 3 mm. Shape: Narrowly oblanceolate; curved. Color: 61B.

*Inflorescence size.*—Length: About 4.5 cm. Diameter: About 7.2 cm.

*Flowers.*—Diameter: About 6 mm. Depth (height): About 3.6 cm.

*Petals.*—Arrangement: Labiate; upper lip hooded; lower lip, a single lobe; lips fused. Length, upper and lower lips: About 2.8 cm. Width, upper lip: About 1 mm. Width, lower lip; About 6 mm. Shape, upper lip: Lanceolate; apex, acute. Shape, lower lip: Narrow oval; apex, aristate. Margin, upper and lower lips: Entire. Texture, upper and lower surfaces: Densely pubescent. Color: When opening, upper and lower surfaces: N66A. Fully opened, upper and lower surfaces: N66B to 67A.

*Sepals.*—Arrangement: Five in a single whorl; fused, tubular. Length: About 8 mm. Width: About 2 mm. Shape: Narrowly lanceolate. Apex: Narrowly acute. Margin: Entire. Texture, upper and lower surfaces: Pubescent. Color: When opening, upper and lower surfaces: 199A; longitudinal stripes, N199A. Fully opened, upper and lower surfaces: 199A; longitudinal stripes, N199A.

*Reproductive organs.*—Stamens: Quantity per flower: Two. Anther shape: Narrowly elliptical. Anther length: About 2.5 mm. Anther color: 61A. Pollen amount: Scarce. Pollen color: 10A. Pistils: Quantity per flower: One. Pistil length: About 3.4 cm. Stigma shape: Cleft. Stigma color: 77A. Style length: About 3.3 cm. Style color: N66D. Ovary color: Light yellow green.

*Seed/fruit.*—Seed and fruit production has not been observed.

Disease/pest resistance: Plants of the new *Monarda* have not been noted to be resistant to pathogens and pests common to *Monarda.*

Garden performance: Plants of the new *Monarda* have exhibited good tolerance to rain and wind and have been observed to be suitable for USDA Zones 5 to 9.

It is claimed:

1. A new and distinct *Monarda* plant named 'Pink Lace' as illustrated and described.

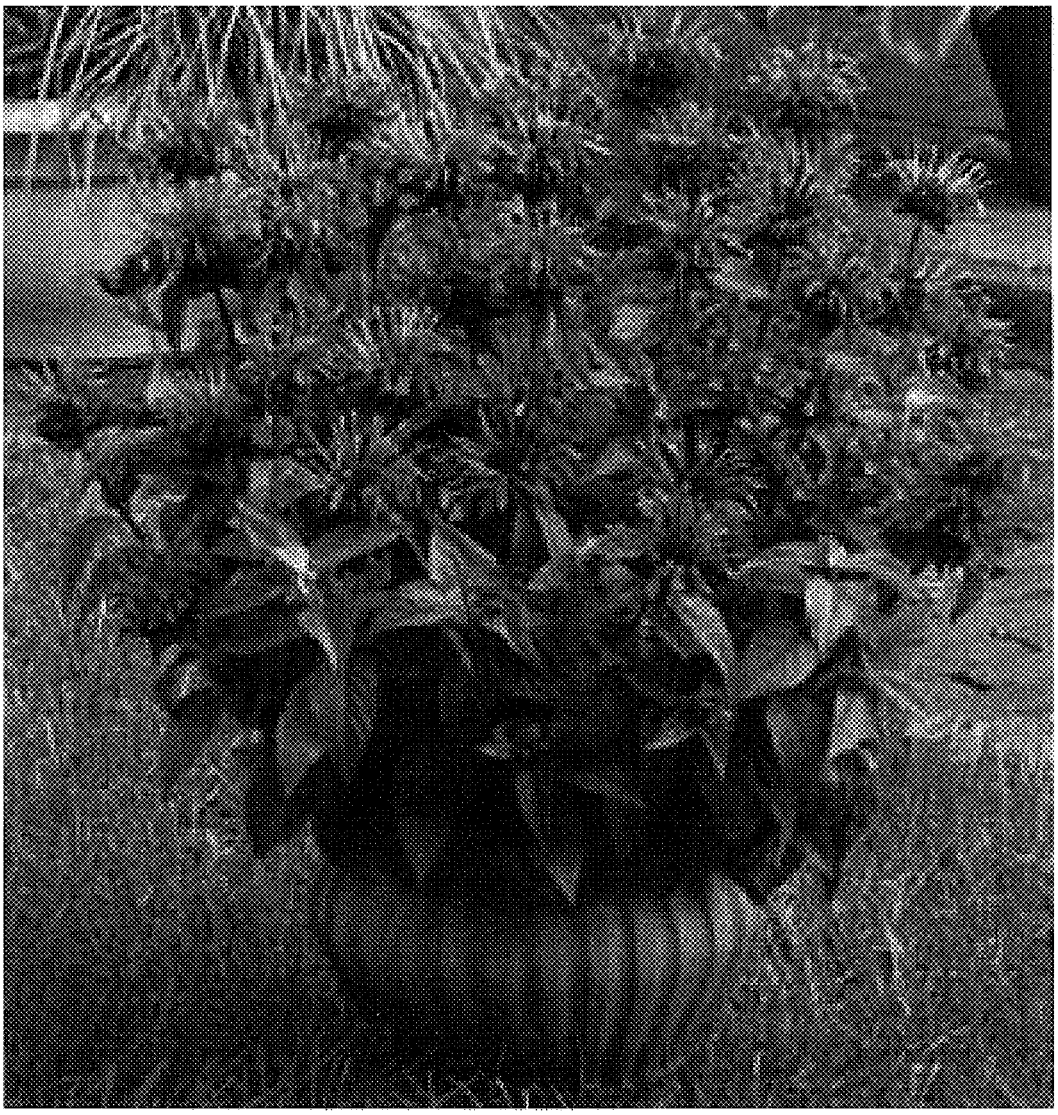

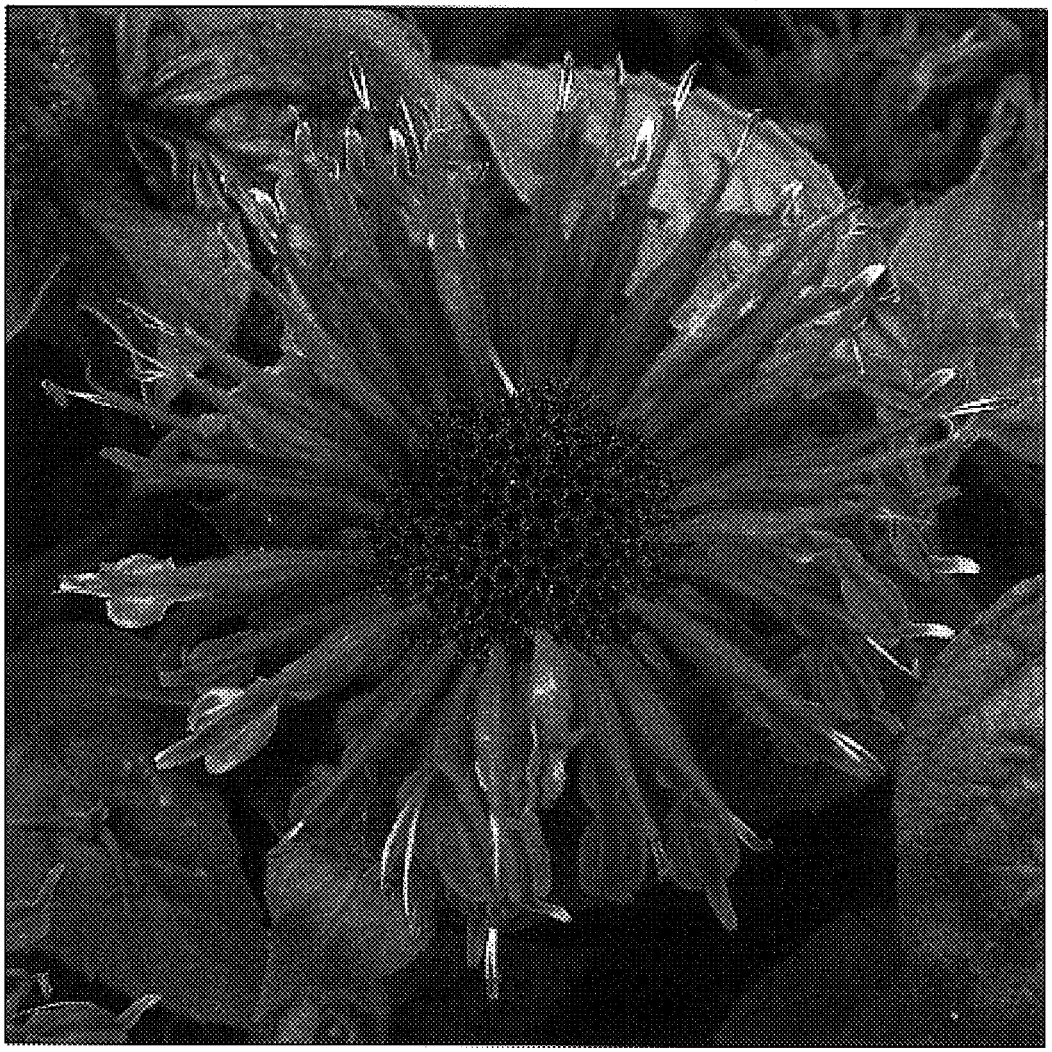
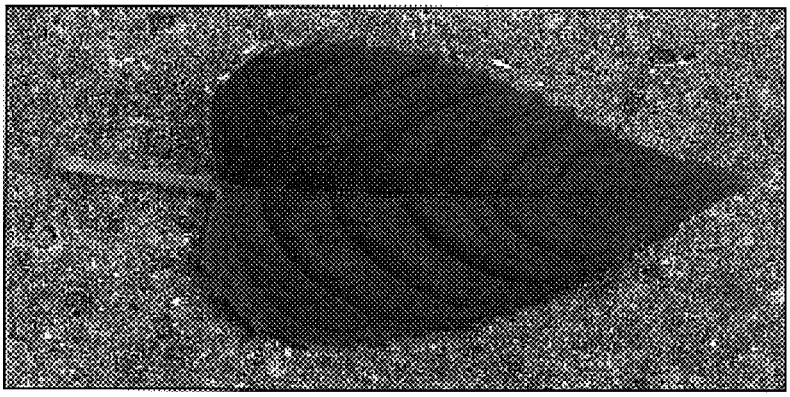

* * * * *